US00PP28110P3

(12) United States Plant Patent
O'Connell

(10) Patent No.: US PP28,110 P3
(45) Date of Patent: Jun. 13, 2017

(54) ***COTYLEDON HYBRID* NAMED 'MINT TRUFFLES'**

(50) Latin Name: ***Cotyledon* hybrid**
Varietal Denomination: Mint Truffles

(71) Applicant: Renee O'Connell, Escondido, CA (US)

(72) Inventor: Renee O'Connell, Escondido, CA (US)

(73) Assignee: Attman Specialty Plants, Inc, Vista, CA (US)

( * ) Notice: Subject to any disclaimer, the term of this patent is extended or adjusted under 35 U.S.C. 154(b) by 43 days.

(21) Appl. No.: 14/756,707

(22) Filed: Oct. 1, 2015

(65) Prior Publication Data

US 2017/0099764 P1 Apr. 6, 2017

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Cotyledon* cultivar named 'Mint Truffles' is disclosed, characterized by a compact morphology, contrasting silvery mint-green leaves margined in crimson. Plants freely offset at an early age, allowing plant to be produced commercially as a clustering 9 cm. Plants, can also be produced in a larger pot size for the landscape. Free offset production at an early age enables faster propagation of the cultivar in the commercial nursery. Plants root quickly and grow vigorously; these characteristics, in combination with the tendency to freely offset at an early age, result in attractive clusters quickly, enhancing production intervals in the commercial environment. The new variety is a *Cotyledon*, part of the Crassulaceae complex that includes *Aeonium, Echeveria, Graptopetalum, Pachyphytum, Sedum* and others. *Cotyledon* is a popular genus, typically produced as container plants for the patio, or as landscape plants.

4 Drawing Sheets

Latin name of the genus and species: *Cotyledon* hybrid. Variety denomination: 'Mint Truffles'.

BACKGROUND OF THE INVENTION

The new cultivar, *Cotyledon* 'Mint Truffles', is a product of a planned breeding program. The new variety originated from a cross pollination of the proprietary, unpatented seed parent *Cotyledon* 'MAC03' with the pollen parent, the proprietary, unpatented pollen parent *Cotyledon* 'ORB06'. The cross pollination was made during August, 2011, in Vista, Calif. at a commercial greenhouse. The new cultivar 'Mint Truffles' was discovered by the inventor, Renee O Connell, in March, 2012, at a commercial greenhouse in Vista, Calif.

Asexual reproduction of the new cultivar 'Mint Truffles' was first performed in Vista, Calif., at a commercial greenhouse, by vegetative terminal cuttings in April, 2012. *Cotyledon* 'Mint Truffles' has since produced multiple generations and has shown that the unique features of this cultivar are stable and reproduced true to type.

SUMMARY OF THE INVENTION

The cultivar 'Mint Truffles' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of *Cotyledon*

'Mint Truffles'. These characteristics in combination distinguish 'Mint Truffles' as a new and distinct *Cotyledon* cultivar:

1. *Cotyledon* 'Mint Truffles' displays a low growing morphology, in combination with silvery mint-green leaves, margined with red.
2. *Cotyledon* 'Mint Truffles' exhibits a compact growth habit, enabling production for small pot sizes, such as 9 cm, as well as for 1, 2 and 5 gallon pots for the landscape.
3. *Cotyledon* 'Mint Truffles' is freely offsetting, at an early age, forming low-growing clusters quickly.
4. *Cotyledon* 'Mint Truffles' is easily and rapidly propagated due to fast rooting, vigorous growth, and prolific offsetting, enhancing production times in the commercial nursery.
5. *Cotyledon* 'Mint Truffles', when planted out in the landscape, continues to have a compact growth; rather than growing tall and lanky, the new cultivar 'Mint Truffles' spreads laterally.

PARENTAL COMPARISON

Plants of the new cultivar 'Mint Truffles' can be compared to plants of the unpatented, proprietary *Cotyledon* 'MAC03', and are similar in most horticultural characteristics. However, plants of the new cultivar 'Mint Truffles' display a more compact morphology, not exhibited by *Cotyledon* 'MAC03'. The new cultivar 'Mint Truffles' is freely offsetting at an early age, in contrast to 'MAC03', which produces few offsets. In addition, the new cultivar 'Mint Truffles' exhibits smaller mint-green leaves with a red margin, in comparison to the larger, lime-green leaves produced by the seed parent *Cotyledon* 'MAC03'. The new cultivar 'Mint Truffles' produces compact plants with many offsets, and grows laterally to form a cluster, in contrast to the seed parent *Cotyledon* 'MAC03', which tends to become tall and leggy with sparse branching.

Plants of the new cultivar 'Mint Truffles' can be compared to plants of pollen parent *Cotyledon* 'ORB06', and are similar in most horticultural characteristics. However, plants of the new cultivar 'Mint Truffles' exhibit early and free offsetting, in contrast to the sparse offsetting produced by the seed parent by *Cotyledon* 'ORB06'. Further, the new cultivar 'Mint Truffles' exhibits smaller mint-green leaves with bright red margins, in contrast to the grayish leaves produced by the pollen parent *Cotyledon* 'ORB06'. Additionally, the new cultivar 'Mint Truffles' can be produced as a 9 cm pot size due to its compact growth and early offsetting, whereas the pollen parent *Cotyledon* 'ORB06' does not make an attractive 9 cm as the leaves and branches are too large, and do not convey the concept of the "small cluster" conveyed by the new cultivar 'Mint Truffles'.

COMMERCIAL COMPARISON

The new cultivar 'Mint Truffles' can be compared to the unpatented commercial variety *Cotyledon orbiculata* v. *orbiculata*. Plants of the *Cotyledon orbiculata* v. *orbiculata* are similar to plants of the new cultivar 'Mint Truffles' in most horticultural characteristics. However, the new cultivar 'Mint Truffles' exhibits a compact form, in contrast to the taller, lanky form exhibited by *Cotyledon orbiculata* v. *orbiculata*. In addition, 'Mint Truffles' forms smaller leaves of mint-green, margined with a contrasting bright red, whereas *Cotyledon orbiculata* v. *orbiculata* forms larger, non-uniform gray to gray white leaves. The new cultivar 'Mint Truffles' is freely offsetting from an early age, forming attractive clusters, whereas *Cotyledon orbiculata* v. *orbiculata* has a upright, lanky, lax growth habit, and does not produce offsets until much older. For this reason, the new cultivar, 'Mint Truffles' due to its quick rooting, freely offsetting and compact growth habit, produces a morphologically aesthetic cluster, thereby enhancing production time in a commercial nursery, in contrast to *Cotyledon orbiculata* v. *orbiculata*.

The new cultivar 'Mint Truffles' can be compared to the unpatented commercial variety *Cotyledon orbiculata* v. 'Macrantha'. Plants of *Cotyledon orbiculata* v. 'Macrantha' are similar to plants of the new cultivar 'Mint Truffles' in most horticultural characteristics. However, the cultivar 'Mint Truffles' exhibits a more compact growth form, growing laterally, rather than vertically, as compared to the lanky, upright growth habit of *Cotyledon orbiculata* 'Macrantha'. In addition, the new cultivar 'Mint Truffles' is freely offsetting from an early age, enhancing the propagation rate, and producing a compact, aesthetically attractive cluster, as compared with *Cotyledon orbiculata* 'Macrantha', which produces offsets sparingly and at an older age.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Cotyledon* plant. All photographs provided by the breeder.

DETAILED BOTANICAL DESCRIPTION

Figure 1:
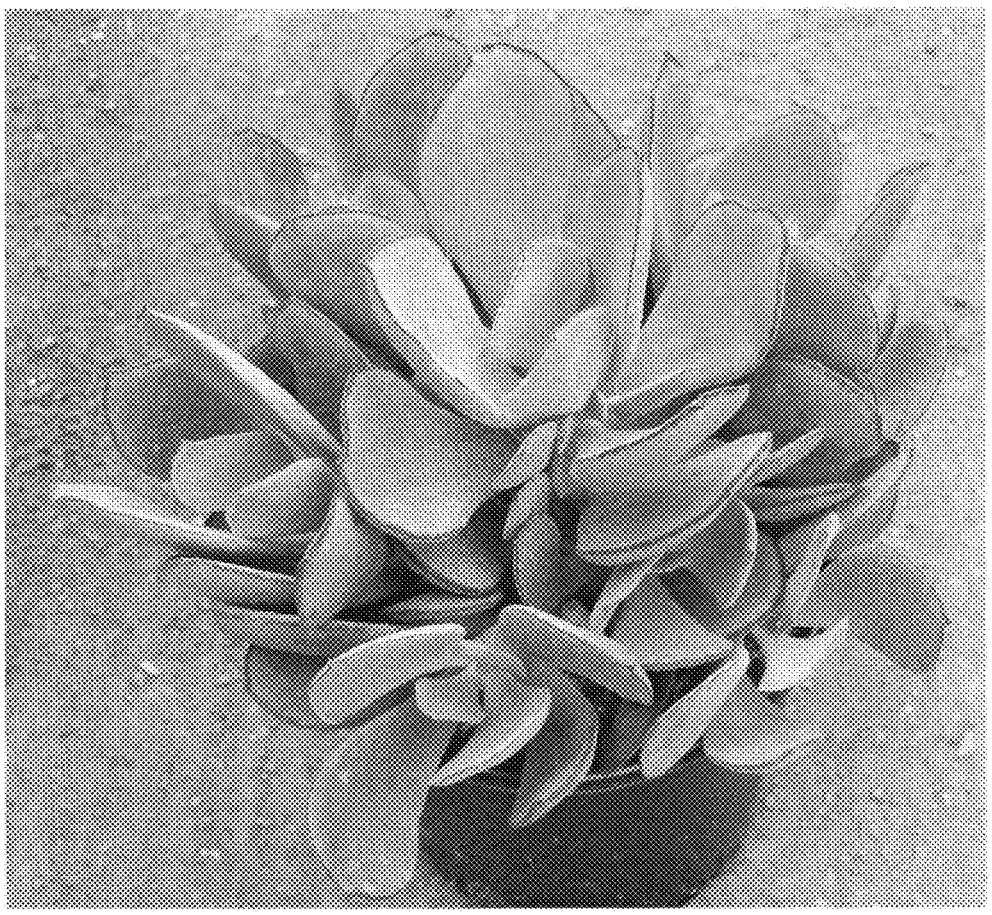
FIG. 1 illustrates in full color a plant typical of *Cotyledon* 'Mint Truffles' grown in full sun (approximately 9000 foot candles) in Vista, Calif.
Figure 2:
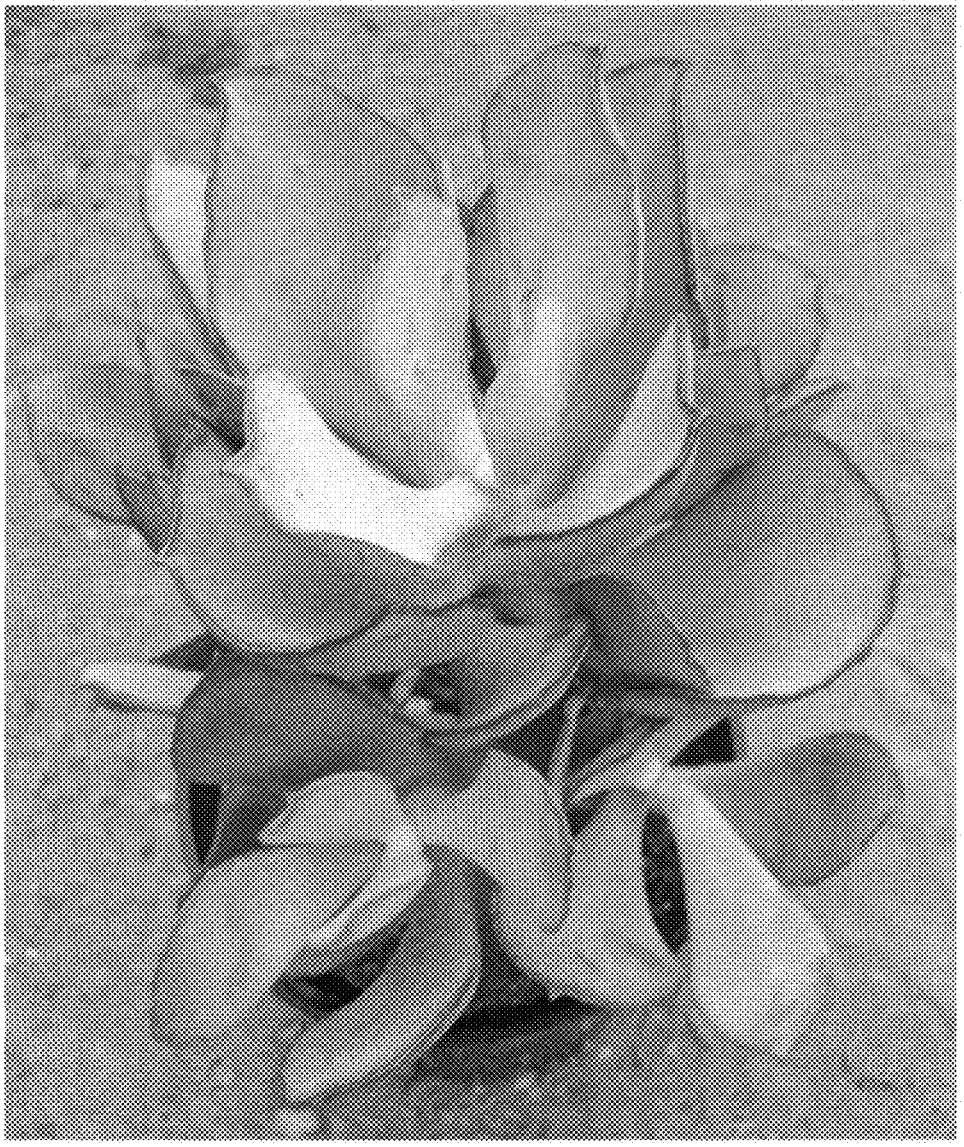
FIG. 2 illustrates in full color a plant typical of *Cotyledon* 'Mint Truffles' grown in a greenhouse (approximately 3500 foot candles) in Vista, Calif.
Figure 3:
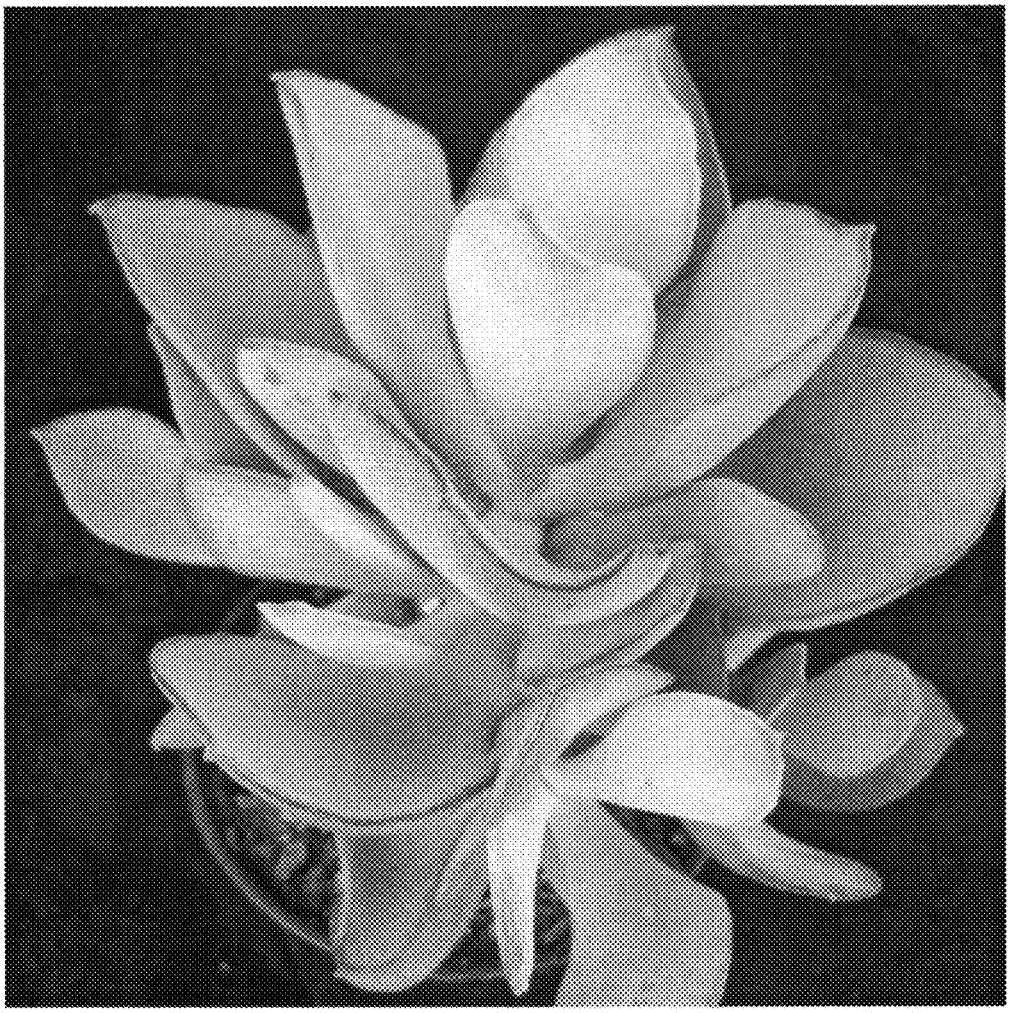
FIG. 3 illustrates in full color a plant typical of *Cotyledon* 'Mint Truffles' grown in a greenhouse (approximately 3500 foot candles) in Vista, Calif. (9 cm pot)
Figure 4:
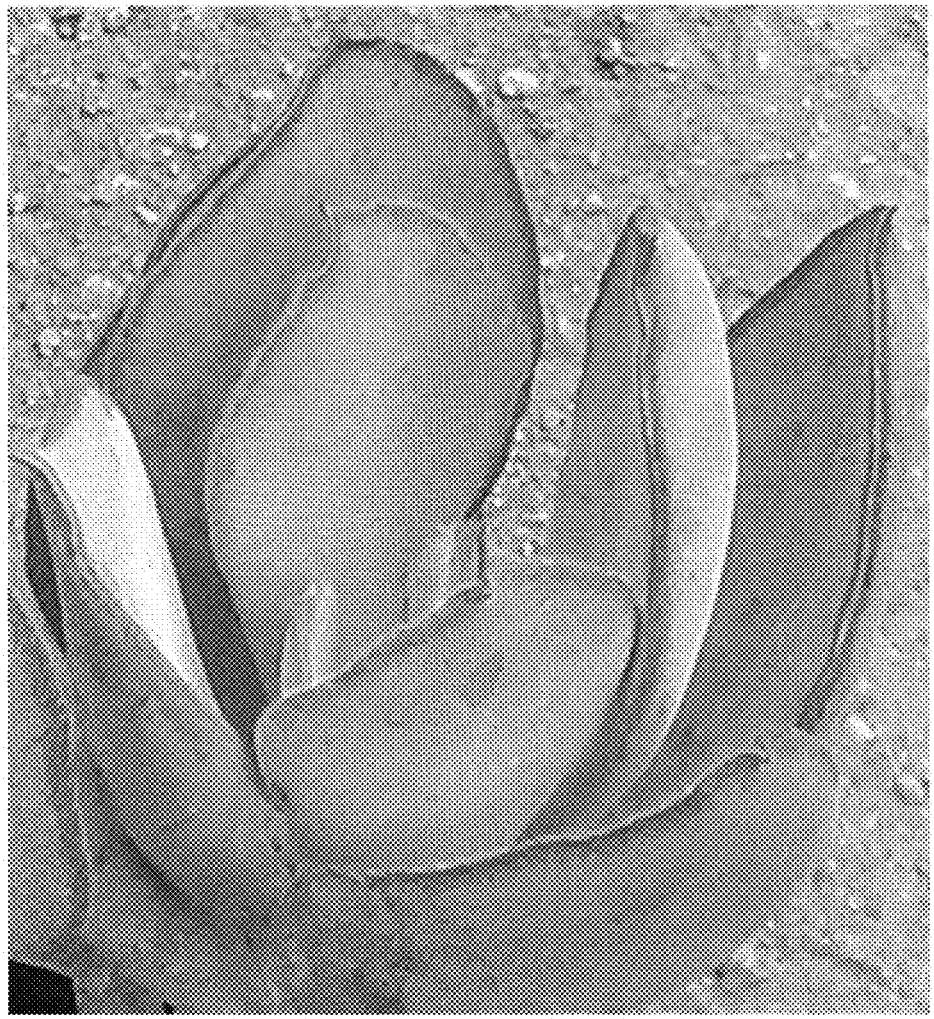
FIG. 4 illustrates in full color a close-up of a branch typical of *Cotyledon* 'Mint Truffles' grown in full sun

In the following description, color references are made to the Panton Process Color System Guide (2014), except where general terms of ordinary dictionary significance are used. The following observations and measurements describe 'Mint Truffles' plants grown in full sun in Vista, Calif. Temperatures ranged from −1° C. to 29° C. night and day. No artificial light, photoperiodic treatments or chemical treatments were given to the plants. Natural light conditions were approximately 9000 fc of light. Measurements and numerical values represent averages of typical plant types.

Botanical classification: *Cotyledon* hybrid 'Mint Truffles'.

Age of the plant described: Approximately 3 months from a cutting.

PROPAGATION

Time to initiate roots: About 11 days at approximately 24° C.

Root description: Fibrous.

Propagation method: Terminal vegetative cuttings.

PLANT

Growth habit: Upright, subshrub branching from base, and continuing to produce offsets between the leaves to form bushy clusters.

Age of plant described: Approximately 3 months from a cutting.

Container size: 15.24 cm.

Height: Approximately 24 cm to top of highest leaf.

Plant spread: Approximately 32 cm.

Growth rate: Moderately fast.

Branching characteristics: Freely offsetting. A 9 cm pot size had 8 branches.

FOLIAGE

Leaf:

*Arrangement*.—Decussate.

*Average length*.—Approximately 8 cm.

*Longest length*.—Approximately 11.3 cm.

*Widest width*.—Approximately 1.35 cm.

*Width at base*.—0.7 cm.

*Shape of blade*.—Oblanceolate.

*Apex*.—Obtuse, mucronate.

*Base*.—Semicircular.

*Margin*.—Entire.

*Texture of top surface*.—Glabrous.

*Texture of bottom surface*.—Glabrous.

*Quantity of leaves per plant*.—Approximately 105, from 11 branches.

*Young foliage upper side*.—Near S 289-6 Pantone & S 289-5 Pantone.

*Young foliage, upper side, apical margin*.—Near S 99-3 Pantone.

*Young foliage upper side, near base*.—Near S 284-6 Pantone.

*Young foliage, under side, towards apex*.—Near S 289-3 Pantone.

*Young foliage, under side, near base*.—Near S 284-8 Pantone.

*Mature foliage upper side*.—Near S 289-5 Pantone.

*Mature foliage, under side*.—Near S 289-4 Pantone.

*Mature foliage, upper side, apical margin*.—Near S 319-1 Pantone.

*Mature foliage, upper side* (9 *cm grown in greenhouse,* 3500 *fc*).—Near S 127-8 Pantone.

*Mature foliage, upper side, margin* (9 *cm grown in greenhouse,* 3500 *fc*).—Near S 137-2 Pantone.

*Venation*.—There is no visual appearance of venation.

FLOWER

Flowering not observed to date.

OTHER CHARACTERISTICS

Fruits and seeds not observed to date.

Temperature tolerance: Tolerates temperatures from approximately −2° C. to 40° C.

Disease/pest resistance: *Cotyledon* 'Mint Truffles' displays the same disease and pest resistance of any other comparable *Cotyledon*.

Drought tolerance: Tolerates at least 4 weeks of high temperatures without supplemental water, showing no serious damage to plant.

What is claimed is:

1. A new and distinct cultivar of *Cotyledon* plant named 'Mint Truffles' as herein illustrated and described.

* * * * *